US008822532B2

(12) United States Patent
Nagai et al.

(10) Patent No.: US 8,822,532 B2
(45) Date of Patent: *Sep. 2, 2014

(54) BIS[THIOHYDRAZIDE AMIDE] COMPOUNDS FOR TREATING LEUKEMIA

(75) Inventors: Masazumi Nagai, Lexington, MA (US); Jianhua Shen, Andover, MA (US)

(73) Assignee: Synta Pharmaceuticals Corp., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/513,449

(22) PCT Filed: Dec. 6, 2010

(86) PCT No.: PCT/US2010/059109
§ 371 (c)(1),
(2), (4) Date: Oct. 23, 2012

(87) PCT Pub. No.: WO2011/069159
PCT Pub. Date: Jun. 9, 2011

(65) Prior Publication Data
US 2013/0035386 A1    Feb. 7, 2013

Related U.S. Application Data

(60) Provisional application No. 61/266,791, filed on Dec. 4, 2009.

(51) Int. Cl.
*A61K 31/28* (2006.01)
*A61P 35/02* (2006.01)
*A61K 31/315* (2006.01)

(52) U.S. Cl.
USPC ........................................................ 514/494

(58) Field of Classification Search
USPC ........................................................ 514/494
See application file for complete search history.

(56) References Cited

U.S. PATENT DOCUMENTS

| | | | |
|---|---|---|---|
| 4,490,080 A | 12/1984 | Kezran | |
| 6,762,204 B2 | 7/2004 | Koya et al. | |
| 6,800,660 B2 | 10/2004 | Koya et al. | |
| 6,825,235 B2 | 11/2004 | Chen et al. | |
| 6,924,312 B2 | 8/2005 | Koya et al. | |
| 7,001,923 B2 | 2/2006 | Koya et al. | |
| 7,037,940 B2 | 5/2006 | Koya et al. | |
| 7,074,952 B2 | 7/2006 | Chen et al. | |
| 7,345,094 B2 | 3/2008 | Koya et al. | |
| 7,368,473 B2 | 5/2008 | Koya et al. | |
| 7,385,084 B2 | 6/2008 | Koya et al. | |
| 7,435,843 B2 | 10/2008 | Chen et al. | |
| 7,579,503 B2 | 8/2009 | Koya et al. | |
| 7,645,904 B2 | 1/2010 | Chen et al. | |
| 7,652,168 B2 | 1/2010 | Chen et al. | |
| 7,671,092 B2 | 3/2010 | Koya et al. | |
| 7,678,832 B2 | 3/2010 | Lunsmann et al. | |
| 7,709,683 B2 | 5/2010 | Chen et al. | |
| 7,750,042 B2 | 7/2010 | Koya et al. | |
| 7,763,658 B2 | 7/2010 | Koya et al. | |
| 7,795,313 B2 | 9/2010 | Koya et al. | |
| 2006/0142386 A1 | 6/2006 | Barsoum | |
| 2006/0142393 A1 | 6/2006 | Sherman et al. | |
| 2006/0167106 A1 | 7/2006 | Zhang et al. | |
| 2007/0088057 A1 | 4/2007 | Lunsmann et al. | |
| 2008/0118562 A1 | 5/2008 | Koya | |
| 2008/0119440 A1 | 5/2008 | Koya | |
| 2008/0176828 A1 | 7/2008 | Williams et al. | |
| 2008/0226588 A1 | 9/2008 | McLeod | |
| 2009/0023736 A1 | 1/2009 | Koya et al. | |
| 2009/0042991 A1 | 2/2009 | Barsoum et al. | |
| 2009/0093538 A1 | 4/2009 | Bertin et al. | |
| 2009/0137682 A1 | 5/2009 | Dahl | |
| 2010/0068174 A1 | 3/2010 | Jacobson | |
| 2010/0081635 A1 | 4/2010 | Chen et al. | |
| 2010/0093828 A1 | 4/2010 | Koya et al. | |
| 2010/0249239 A1 | 9/2010 | Lunsmann et al. | |
| 2010/0280075 A1 | 11/2010 | Koya et al. | |
| 2010/0324143 A1 | 12/2010 | Koya et al. | |
| 2011/0098476 A1 | 4/2011 | Chen et al. | |
| 2011/0196025 A1 | 8/2011 | Kostik et al. | |
| 2011/0245262 A1 | 10/2011 | Sun et al. | |
| 2011/0245577 A1 | 10/2011 | Koya | |
| 2011/0288162 A1 | 11/2011 | Masazumi et al. | |
| 2011/0294814 A1 | 12/2011 | Kowalczyk-Prezewloka et al. | |
| 2011/0294877 A1* | 12/2011 | Masazumi et al. | ............ 514/499 |
| 2011/0294895 A1 | 12/2011 | Lunsmann et al. | |
| 2012/0035266 A1 | 2/2012 | Koya et al. | |
| 2012/0065206 A1 | 3/2012 | Jiang et al. | |
| 2012/0065235 A1 | 3/2012 | Sun et al. | |

FOREIGN PATENT DOCUMENTS

| | | | | |
|---|---|---|---|---|
| WO | WO 2006009940 A1 * | 1/2006 | ............ | C07C 327/56 |
| WO | WO-2008/024299 A2 | 4/2008 | | |
| WO | WO-2010/048293 A1 | 4/2010 | | |

OTHER PUBLICATIONS

El-Asmy et al., Structural studies on cadmium(II), cobalt(II), copper(II), nickel(II) and zinc(II) complexes of 1-malonyl-bis(4-phenylthiosemicarbazide, Transition Met. Chem., 15:12-15, 1990.*
Foley et al., The Oxidative Stress Inducer Elesclomol (Formerly STA-4783) Enhances the in Vivo Efficacy of Multiple Anti-Cancer Therapies in Mouse Tumor Models, Synta Pharmaceuticals Corp., Poster presentation, Oct. 24, 2007.*
Creutzig et al., Improved Treatment Results in High-Risk Pediatric Acute Myeloid Leukemia Patients After Intensification With High-Dose Cytarabine and Mitoxantrone: Results of Study Acute Myeloid Leukemia-Berlin-Frankfurt-Munster 93, Journal of Clinical Oncology, 19(10):2705-2713, 2001.*
Tsimberidou et al., The Prognostic Significance of Cytokine Levels in Newly Diagnosed Acute Myeloid Leukemia and High-risk Myelodysplastic Syndromes, Cancer, 113:7, 1605-1613, 2008.*
Chow, et al., Abstract #2736, "Antileukemic Effects of the Novel Agent Elesclomol" American Society of Hematology (ASH) ASH 2009 Annual Meeting, Dec. 5, 2009.

* cited by examiner

*Primary Examiner* — Jeffrey S. Lundgren
*Assistant Examiner* — Zenab Olabowale
(74) *Attorney, Agent, or Firm* — McCarter & English, LLP; Steven G. Davis (57) ABSTRACT

Certain bis[thio-hydrazide amide]-related compounds are found to be surprisingly effective at treating with leukemia, e.g., acute myeloid leukemia (AML). Methods of treating a subject with AML including administering bis[thio-hydrazide amide]-related compounds described herein, are disclosed.

14 Claims, 4 Drawing Sheets

BIS[THIOHYDRAZIDE AMIDE] COMPOUNDS FOR TREATING LEUKEMIA

CROSS-REFERENCE TO RELATED PATENT APPLICATIONS

This application claims priority to U.S. Provisional Application No. 61/266,791, filed Dec. 4, 2009, incorporated herein by reference in its entirety.

BACKGROUND OF THE INVENTION

Relapsed and refractory hematologic acute myeloid leukemia (AML) has a poor response to standard therapy and is associated with a poor prognosis. For example, relapsed AML is a highly aggressive and resistant disease, particularly when associated with a first complete response (CR) duration of less than 12 months. Rates of second remission after such a rapid relapse are lower (25-30% vs. 60%), and remissions are briefer. A recent study from the leukemia group at Princess Margaret Hospital demonstrated that the overall response to reinduction chemotherapy was approximately 50%, but the patients relapsed shortly thereafter if not transplanted. Patients over age 60, with poor risk cytogenetics and/or over 80% blasts in the marrow at reinduction had particularly poor responses to reinduction with a CR rate of approximately 20%. Older patients in particular tend to do poorly with reinduction due to a combination of co-morbid conditions and cumulative hematologic and nonhematologic toxicity. Allogeneic bone marrow transplantation is the only curative option for patients obtaining a second remission, but this treatment modality is not universally available due to lack of related or unrelated donors, patient's age, or the patient's co-morbidities.

Several studies have shown that elevated levels of LDH are a strong prognostic factor in patients with AML, correlating with poor prognosis and response to therapy as well as to an increased likelihood of tumor lysis syndrome.

Thus, there is an urgent need for new agents in relapsed and refractory hematologic malignancies such as acute leukemia. In elderly patients, where the tolerance of aggressive induction therapy is often poor and curative options such as bone marrow transplantation are not available, the need for effective non-aggressive drug regimens for AML is even greater.

SUMMARY OF THE INVENTION

It has been found that certain bis[thio-hydrazide amide]-related compounds are surprisingly effective at treating leukemia, e.g., acute myeloid leukemia (AML). A method of treating a subject with AML includes the step of administering to the subject bis[thio-hydrazide amide]-related compounds described herein.

In one embodiment, the invention includes the use of bis [thio-hydrazide amide]-related compounds described herein for the manufacture of a medicament for AML.

In one embodiment, the invention includes methods of treating a subject having acute myeloid leukemia (AML), comprising administering to the subject an effective amount of a compound represented by Structural Formula (I), otherwise known as elesclomol:

or a prodrug, isomer, ester, salt, hydrate, solvate, polymorph or deprotonated form thereof complexed, coordinated or chelated to a transition metal cation. Advantageously, the subject has normal-to-low levels of LDH, e.g., LDH (total)≤0.8× ULN.

In one embodiment, the invention includes methods of treating a subject having acute myeloid leukemia (AML), comprising administering to the subject an effective amount of a transition metal complex of the compound of structural formula (I) or a deprotonated form thereof described herein, or a pharmaceutically acceptable salt thereof. In one embodiment, the transition metal complex is represented by the following structural formula:

wherein X is a transition metal cation with a +2 charge. More specifically, the transition metal cation is $Ni^{2+}$, $Cu^{2+}$, $Co^{2+}$, $Fe^{2+}$, $Zn^{2+}$, $Pt^{2+}$ or $Pd^{2+}$. In another more specific embodiment, the transition metal cation is $Ni^{2+}$ or $Cu^{2+}$. Even more specifically, the transition metal cation is $Cu^{2+}$.

In one embodiment, the invention includes methods of treating a subject with AML, comprising administering to the subject an effective amount of bis[thio-hydrazide amide]-related compounds described herein, or a pharmaceutically acceptable salt thereof, in combination with γ-radiation.

In one embodiment, the invention includes methods of treating a subject with AML, comprising administering to the subject an effective amount of bis[thio-hydrazide amide]-related compounds described herein, or a pharmaceutically acceptable salt thereof, in combination with an effective amount of cytarabine (also known as Ara-C) and γ-radiation.

In another embodiment, the invention includes methods of identifying a compound for treating a subject with acute myeloid leukemia (AML) comprising testing the compound to determine whether the compound can increase the level of reactive oxygen species (ROS) in a cancer cell. A compound that increases the level of ROS in a cancer cell can be used for treating AML.

Another embodiment is directed to methods of identifying a compound for treating a subject with acute myeloid leukemia (AML) comprising testing the compound to determine whether the compound can decrease the level of GSH in a cancer cell. A compound that decreases the level of GSH in a cancer cell can be used for treating AML.

Another embodiment is directed to a method of identifying a compound for treating a subject with acute myeloid leukemia (AML) comprising testing the compound to determine whether the compound can dissipate mitochondrial membrane potential in a cancer cell. A compound that causes the dissipation of mitochondrial membrane potential in a cancer cell can be used for treating AML. In another embodiment, the method of identifying the compound for treating a subject with acute myeloid leukemia (AML) is as described in Example 2.

DETAILED DESCRIPTION OF THE INVENTION

In order that the present invention may be more readily understood, certain terms are first defined. In addition, it should be noted that whenever a value or range of values of a parameter are recited, it is intended that values and ranges intermediate to the recited values are also intended to be part of this invention.

Definitions

The articles "a", "an" and "the" are used herein to refer to one or to more than one (i.e. to at least one) of the grammatical object of the article unless otherwise clearly indicated by contrast. By way of example, "an element" means one element or more than one element.

The term "including" is used herein to mean, and is used interchangeably with, the phrase "including but not limited to".

The term "or" is used herein to mean, and is used interchangeably with, the term "and/or," unless context clearly indicates otherwise.

The term "such as" is used herein to mean, and is used interchangeably, with the phrase "such as but not limited to".

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about.

The recitation of a listing of chemical group(s) in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

As used herein, the term "subject" refers to human and non-human animals, including veterinary subjects. The term "non-human animal" includes all vertebrates, e.g., mammals and non-mammals, such as non-human primates, mice, rabbits, sheep, dog, cat, horse, cow, chickens, amphibians, and reptiles. In a preferred embodiment, the subject is a human and may be referred to as a patient.

As used herein, the terms "treat," "treating" or "treatment" refer, preferably, to an action to obtain a beneficial or desired clinical result including, but not limited to, alleviation or amelioration of one or more signs or symptoms of a disease or condition, diminishing the extent of disease, stability (i.e., not worsening) state of disease, amelioration or palliation of the disease state, diminishing rate of or time to progression, and remission (whether partial or total), whether detectable or undetectable. "Treatment" can also mean prolonging survival as compared to expected survival in the absence of treatment.

A "therapeutically effective amount" is that amount sufficient to treat a disease in a subject. A therapeutically effective amount can be administered in one or more administrations.

By "diagnosing" and the like, as used herein, refers to a clinical or other assessment of the condition of a subject based on observation, testing, or circumstances for identifying a subject having a disease, disorder, or condition based on the presence of at least one indicator, such as a sign or symptom of the disease, disorder, or condition. Typically, diagnosing using the method of the invention includes the observation of the subject for multiple indicators of the disease, disorder, or condition in conjunction with the methods provided herein. Diagnostic methods provide an indicator that a disease is or is not present. A single diagnostic test typically does not provide a definitive conclusion regarding the disease state of the subject being tested.

The terms "administer", "administering" or "administration" include any method of delivery of a pharmaceutical composition or agent into a subject's system or to a particular region in or on a subject. In certain embodiments of the invention, an agent is administered intravenously, intramuscularly, subcutaneously, intradermally, intranasally, orally, transcutaneously, or mucosally. In a preferred embodiment, an agent is administered intravenously. Administering an agent can be performed by a number of people working in concert. Administering an agent includes, for example, prescribing an agent to be administered to a subject and/or providing instructions, directly or through another, to take a specific agent, either by self-delivery, e.g., as by oral delivery, subcutaneous delivery, intravenous delivery through a central line, etc.; or for delivery by a trained professional, e.g., intravenous delivery, intramuscular delivery, intratumoral delivery, etc.

As used herein, the term "survival" refers to the continuation of life of a subject which has been treated for a disease or condition, e.g., cancer.

As used herein, the term "recur" refers to the re-growth of tumor or cancerous cells in a subject in whom primary treatment for the tumor has been administered. The tumor may recur in the original site or in another part of the body. In one embodiment, a tumor that recurs is of the same type as the original tumor for which the subject was treated. For example, if a subject had an ovarian cancer tumor, was treated and subsequently developed another ovarian cancer tumor, the tumor has recurred. In addition, a cancer can recur in or metastasize to a different organ or tissue than the one where it originally occurred.

As used herein, the terms "identify" or "select" refer to a choice in preference to another. In other words, to identify a subject or select a subject is to pick out that particular subject.

As used herein, the term "benefit" refers to something that is advantageous or good, or an advantage. Similarly, the term "benefiting", as used herein, refers to something that improves or advantages. For example, a subject will benefit from treatment if they exhibit a decrease in at least one sign or symptom of a disease or condition (e.g., tumor shrinkage, decrease in tumor burden, inhibition or decrease of metastasis, improving quality of life ("QOL"), if there is a delay of time to progression ("TTP"), if there is an increase of overall survival ("OS"), etc.), or if there is a slowing or stopping of disease progression (e.g., halting tumor growth or metastasis, or slowing the rate of tumor growth or metastasis). A benefit can also include an improvement in quality of life, or an increase in survival time or progression free survival.

As used herein, the term "obtaining" is understood herein as manufacturing, purchasing, or otherwise coming into possession of.

"bis[thio-hydrazide amide]-related compounds" include bis[thio-hydrazide amide] represented by Structural Formula (I):

(I)

or a prodrug, isomer, ester, salt, hydrate, solvate, polymorph or deprotonated form thereof complexed, coordinated or chelated to a transition metal cation. One example of a compound of this type is represented by Structural Formula (II):

(II)

or a prodrug, isomer, ester, salt, hydrate, solvate, or polymorph thereof, wherein X is a transition metal cation having a +2 charge.

As used herein, "complexed" means that the bis[thiohydrazide amide] or a prodrug, isomer, ester, salt, hydrate, solvate, polymorph or deprotonated form thereof attaches to the transition metal ion through one or more coordinate covalent bonds or coordination bonds.

As used herein, "chelated" means that the bis[thiohydrazide amide] or a prodrug, isomer, ester, salt, hydrate, solvate, polymorph or deprotonated form thereof binds to the transition metal ion at two or more attachment points through coordinate covalent bonds or coordination bonds.

As used herein, "coordinate", "coordinated", "coordinate covalent bond" and "coordination bond" have the meanings that are commonly known to one of ordinary skill in the art.

As used herein, a "deprotonated form" of bis[thiohydrazide amide] refers to a molecule wherein one or more protons from the bis[thiohydrazide amide] or a prodrug, isomer, ester, salt, hydrate, solvate or polymorph thereof were removed. For example, a deprotonated form of the bis[thiohydrazide amide] of Structural Formula (I) is represented by the following structural formula:

(Ia)

A "transition metal cation" refers to a positively charged ion of a metal in Groups 3-12 of the Periodic Table. Examples include $Ni^{2+}$, $Cu^+$, $Cu^{2+}$, $Co^{2+}$, $Co^{3+}$, $Fe^{2+}$, $Fe^{3+}$, $Zn^{2+}$, $Pt^{2+}$, $Pd^{2+}$, $V^{4+}$, $V^{5+}$, $Cr^{2+}$, $Cr^{3+}$, $Cr^{4+}$, $Mn^{2+}$, $Mn^{3+}$, $Mn^{4+}$ and $Mn^{5+}$. In a specific embodiment, the transition metal cations have a +2 charge. Examples include $Ni^{2+}$, $Cu^{2+}$, $Co^{2+}$, $Fe^{2+}$, $Zn^{2+}$, $Pt^{2+}$ and $Pd^{2+}$. In a specific embodiment, the transition metal cation is $Cu^+$, $Cu^{2+}$ or $Ni^{2+}$. In a more specific embodiment, the transition metal cation is $Cu^{2+}$. The molar ratio of bis[thiohydrazide amide] or a prodrug, isomer, ester, salt, hydrate, solvate, polymorph or a deprotonated form thereof to transition metal cation recited in this paragraph is, for example, equal to or greater than 0.5 and equal to or less than 2.0 (i.e. $0.5 \leq ratio \leq 2.0$) or 1:1.

As used herein, the term "solvate" means a compound of the present invention described herein, that further includes a stoichiometric or non-stoichiometric amount of solvent bound by non-covalent intermolecular forces.

As used herein, the term "hydrate" means a compound of the present invention described herein, that further includes a stoichiometric or non-stoichiometric amount of water bound by non-covalent intermolecular forces.

As used herein, the term "prodrug" means a derivative of a compound that can hydrolyze, oxidize, or otherwise react under biological conditions (in vitro or in vivo) to provide a compound of this invention. Prodrugs may become active upon such reaction under biological conditions, or they may have activity in their unreacted forms.

"Treating a subject with a cancer" includes achieving, partially or substantially, one or more of the following: arresting the growth or spread of a cancer, reducing the extent of a cancer (e.g., reducing size of a tumor or reducing the number of affected sites), inhibiting the growth rate of a cancer, ameliorating or improving a clinical symptom or indicator associated with a cancer (such as tissue or serum components) and/or reducing the likelihood of the cancer recurring once it has been removed or gone into remission.

As used herein, a "microtubulin stabilizer" means an anticancer agent which acts by arresting cells in the G2-M phases due to stabilization of microtubules. Agents which are microtubulin stabilizers can be used in combination with the compounds of the invention to treat patients having a proliferative disorder such as cancer, or to reduce the likelihood of the reoccurrence of a proliferative disorder such as cancer. Examples of microtubulin stabilizers include taxol and taxol analogs. Additional examples of microtubulin stabilizers included without limitation the following marketed drugs and drugs in development: Discodermolide (also known as NVP-XX-A-296); Epothilones (such as Epothilone A, Epothilone B, Epothilone C (also known as desoxyepothilone A or dEpoA); Epothilone D (also referred to as KOS-862, dEpoB, and desoxyepothilone B); Epothilone E; Epothilone F; Epothilone B N-oxide; Epothilone A N-oxide; 16-aza-epothilone B; 21-aminoepothilone B (also known as BMS-310705); 21-hydroxyepothilone D (also known as Desoxyepothilone F and dEpoF), 26-fluoroepothilone); FR-182877 (Fujisawa, also known as WS-9885B), BSF-223651 (BASF, also known as ILX-651 and LU-223651); AC-7739 (Ajinomoto, also known as AVE-8063A and CS-39. HCl); AC-7700 (Ajinomoto, also known as AVE-8062, AVE-8062A, CS-39-L-Ser.HCl, and RPR-258062A); Fijianolide B; Laulimalide; Caribaeoside; Caribaeolin; Taccalonolide; Eleutherobin; Sarcodictyin; Laulimalide; Dictyostatin-1; Jatrophane esters; and analogs and derivatives thereof.

As used herein, a "microtubulin inhibitor" means an anticancer agent which acts by inhibiting tubulin polymerization or microtubule assembly. Agents which are microtubulin inhibitors can be used in combination with the compounds of the invention to treat patients having a cancer, or to reduce the likelihood the reoccurrence of cancer. Examples of microtubulin inhibitors include without limitation the following marketed drugs and drugs in development: Erbulozole (also known as R-55104); Dolastatin 10 (also known as DLS-10 and NSC-376128); Mivobulin isethionate (also known as CI-980); Vincristine; NSC-639829; ABT-751 (Abbot, also known as E-7010); Altorhyrtins (such as Altorhyrtin A and Altorhyrtin C); Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9); Cemadotin hydrochloride (also known as LU-103793 and NSC-D-669356); Auristatin PE (also known as NSC-654663); Soblidotin (also known as TZT-1027), LS-4559-P (Pharmacia, also known as LS-4577); LS-4578 (Pharmacia, also known as LS-477-P); LS-4477 (Pharmacia), LS-4559 (Pharmacia); RPR-112378 (Aventis); Vincristine sulfate; DZ-3358 (Daiichi); GS-164 (Takeda); GS-198 (Takeda); KAR-2 (Hungarian Academy of Sciences); SAH-49960 (Lilly/Novartis); SDZ-268970 (Lilly/Novartis); AM-97 (Armad/Kyowa Hakko); AM-132 (Armad); AM-138 (Armad/Kyowa Hakko); IDN-5005 (Indena); Cryptophycin 52 (also known as LY-355703); Vitilevuamide; Tubulysin A; Canadensol; Centaureidin (also known as NSC-I06969); T-138067 (Tularik, also known as T-67, TL-138067 and TI-138067); COBRA-1 (Parker Hughes Institute, also known as DDE-261 and WHI-261); H10 (Kansas State University); H16 (Kansas State University); Oncocidin A1 (also known as BTO-956 and DIME); DDE-313 (Parker Hughes Institute); SPA-2 (Parker Hughes Institute); SPA-1 (Parker Hughes Institute, also known as SPIKET-P); 3-IAABU (Cytoskeleton/Mt. Sinai School of Medicine, also known as MF-569); Narcosine (also known as NSC-5366); Nascapine, D-24851 (Asta Medica), A-105972 (Abbott); Hemiasterlin; 3-BAABU (Cytoskeleton/Mt. Sinai School of Medicine, also known as MF-191); TMPN (Arizona State University); Vanadocene acetylacetonate; T-138026 (Tularik); Monsatrol; Inanocine (also known as NSC-698666); 3-IAABE (Cytoskeleton/Mt. Sinai School of Medicine); A-204197 (Abbott); T-607 (Tularik, also known as T-900607); RPR-115781 (Aventis); Eleutherobins (such as Desmethyleleutherobin, Desaetyleleutherobin, Isoeleutherobin A, and Z-Eleutherobin); Halichondrin B; D-64131 (Asta Medica); D-68144 (Asta Medica); Diazonamide A; A-293620 (Abbott); NPI-2350 (Nereus); TUB-245 (Aventis); A-259754 (Abbott); Diozostatin; (−)-Phenylahistin (also known as NSCL-96F037); D-68838 (Asta Medica); D-68836 (Asta Medica); Myoseverin B; D-43411 (Zentaris, also known as D-81862); A-289099 (Abbott); A-318315 (Abbott); HTI-286 (also known as SPA-110, trifluoroacetate salt) (Wyeth); D-82317 (Zentaris); D-82318 (Zentaris); SC-12983 (NCI); Resverastatin phosphate sodium; BPR-0Y-007 (National Health Research Institutes); SSR-250411 (Sanofi); Combretastatin A4; and analogs and derivatives thereof.

Paclitaxel also referred to as "Taxol®", is a well-known anti-cancer drug which acts by enhancing and stabilizing microtubule formation. Many analogs of paclitaxel are known, including docetaxel and cabazitaxel. Docetaxel is also referred to as "Taxotere®". Formulations of paclitaxel, such as nab-paclitaxel (Abraxane®), are well-known. Other paclitaxel analogs have the basic taxane skeleton as a common structure feature and have also been shown to have the ability to arrest cells in the G2-M phases due to stabilization of microtubules. A wide variety of substituents can decorate the taxane skeleton without adversely affecting biological activity. It is also known that zero, one or both of the cyclohexane rings of a paclitaxel analog can have a double bond at the indicated positions.

The precise amount of compound administered to a subject will depend on the severity of the disease or condition and on the characteristics of the subject, such as general health, age, sex, body weight and tolerance to drugs. The skilled artisan will be able to determine appropriate dosages depending on these and other factors. Effective amounts of the disclosed compounds typically range between about 1 mg/M$^2$ per day and about 10 grams/M$^2$ per day, and preferably between 10 mg/M$^2$ per day and about 5 grams/M$^2$. In some embodiments, effective amounts of the disclosed compounds include microgram to milligram amounts of the compound per kilogram of subject or sample weight (e.g., about 1 µg/kg to about 500 mg/kg, about 500 µg/kg to about 250 mg/kg, about 1 mg/kg to about 100 mg/kg, about 10 mg/kg to about 50 mg/kg, and the like). When co-administered with another anti-cancer agent for the treatment of cancer, e.g., a microtubulin inhibitor, an "effective amount" of the second anti-cancer agent will depend on the type of drug used. Suitable dosages are known for approved anti-cancer agents and can be adjusted by the skilled artisan according to the condition of the subject, the type of cancer being treated and the compound of the invention being used.

The frequency and dosage will also vary according to factors specific for each patient depending on the specific therapy (e.g., therapeutic or prophylactic agents) administered, the severity of the disorder, disease, or condition, the route of administration, as well as age, body, weight, response, and the past medical history of the patient. Effective doses may be extrapolated from dose-response curves derived from in vitro or animal model test systems, and by achieving certain blood levels of the drug, or by monitoring change in appropriate biomarkers that serve as a surrogate for efficacy. Suitable regiments can be selected by one skilled in the art by considering such factors and by following, for example, dosages reported in the literature and recommended in the *Physician's Desk Reference* (57th ed., 2003).

The dosages of prophylactic or therapeutic agents other than compounds of the invention, which have been or are currently being used to prevent, treat, manage, or proliferative disorders, such as cancer, or one or more symptoms thereof can be used in combination therapies. Preferably, dosages lower than those which have been or are currently being used to prevent, treat, manage, or ameliorate a proliferative disorder, or one or more symptoms thereof, are used in combination therapies. The recommended dosages of agents currently used for the prevention, treatment, management, or amelioration of a proliferative disorders, such as cancer, or one or more symptoms thereof, can obtained from any reference in the art including, but not limited to, Hardman et al., eds., 1996, Goodman & Gilman's The Pharmacological Basis Of Basis Of Therapeutics 9$^{th}$ Ed, Mc-Graw-Hill, New York; Physician's Desk Reference (PDR) 57$^{th}$ Ed., 2003, Medical Economics Co., Inc., Montvale, N.J.

In certain embodiments, when the compounds of the invention are administered in combination with another therapy, the therapies (e.g., prophylactic or therapeutic agents) are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In one embodiment, two or more therapies (e.g., prophylactic or therapeutic agents) are administered within the same patent visit.

In certain embodiments, one or more compounds of the invention and one or more other the therapies (e.g., prophylactic or therapeutic agents) are cyclically administered. Cycling therapy involves the administration of a first therapy (e.g., a first prophylactic or therapeutic agents) for a period of time, followed by the administration of a second therapy (e.g., a second prophylactic or therapeutic agents) for a period of time, followed by the administration of a third therapy (e.g., a third prophylactic or therapeutic agents) for a period of time and so forth, and repeating this sequential administration, i.e., the cycle in order to reduce the development of resistance to one of the agents, to avoid or reduce the side effects of one of the agents, and/or to improve the efficacy of the treatment.

In certain embodiments, administration of the same compound of the invention may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same prophylactic or therapeutic agent may be repeated and the administration may be separated by at least at least 1 day, 2 days, 3 days, 5 days, 10 days, 15 days, 30 days, 45 days, 2 months, 75 days, 3 months, or 6 months.

It has been found that certain bis[thio-hydrazide amide]-related compounds are surprisingly effective at treating subjects with acute myeloid leukemia (AML). A method of treating a subject with AML includes the step of administering to the subject bis[thio-hydrazide amide]-related compounds described herein.

In one embodiment, the invention includes the use of bis[thio-hydrazide amide]-related compounds described herein for the manufacture of a medicament for AML.

In one embodiment, the invention includes methods of treating a subject having acute myeloid leukemia (AML), comprising administering to the subject an effective amount of a compound represented by Structural Formula (I):

(I)

or a prodrug, isomer, ester, salt, hydrate, solvate, polymorph or deprotonated form thereof complexed, coordinated or chelated to a transition metal cation.

In one embodiment, the invention includes methods of treating a subject having acute myeloid leukemia (AML), comprising administering to the subject an effective amount of a transition metal complex of the compound of structural formula (I) or a deprotonated form thereof described herein, or a pharmaceutically acceptable salt thereof. In one embodiment, the transition metal complex is represented by the following structural formula:

(II)

wherein X is a transition metal cation with a +2 charge. More specifically, the transition metal cation is $Ni^{2+}$, $Cu^{2+}$, $Co^{2+}$, $Fe^{2+}$, $Zn^{2+}$, $Pt^{2+}$ or $Pd^{2+}$. In another more specific embodiment, the transition metal cation is $Ni^{2+}$ or $Cu^{2+}$. Even more specifically, the transition metal cation is $Cu^{2+}$.

In one embodiment, the invention includes methods of treating a subject with AML, comprising administering to the subject an effective amount of bis[thio-hydrazide amide]-related compounds described herein, or a pharmaceutically acceptable salt thereof, in combination with γ-radiation.

In one embodiment, the invention includes methods of treating a subject with AML, comprising administering to the subject an effective amount of bis[thio-hydrazide amide]-related compounds described herein, or a pharmaceutically acceptable salt thereof, in combination with an effective amount of cytarabine (also known as Ara-C) and γ-radiation.

In another embodiment, the invention includes methods of identifying a compound for treating a subject with acute myeloid leukemia (AML) comprising testing the compound to determine whether the compound can increase the level of reactive oxygen species (ROS) in a cancer cell. A compound that increases the level of ROS in a cancer cell can be used for treating AML. The level of reactive oxygen species in a cell can, for example, be analyzed by using carboxy-dichlorofluorescin or dihydrorhodamine. Other known methods for analyzing the level of ROS in a cell can also be used. For example, the level of reactive oxygen species can be analyzed by using OxiSelect™ ROS assay kit (catalog #STA-342, Cell Biolabs, Inc., San Diego, Calif.). For compounds that increase the level of ROS, the method optionally further comprises the step of testing the compound in a cell assay using AML cell lines. Examples of AML cell lines include, but are not limited to, OCI-AML2, OCI-AML5, OCI-M2 and MV4-11 cell lines. The cell assay can be a cytotoxicity assay, an assay analyzing the mitochondrial membrane potential (MMP), an assay analyzing the level of glutathione (GSH), or a combination thereof.

Another embodiment is directed to methods of identifying a compound for treating a subject with acute myeloid leukemia (AML) comprising testing the compound to determine whether the compound can decrease the level of GSH in a cancer cell. A compound that decreases the level of GSH in a cancer cell can be used for treating AML. The level of GSH in a cell can, for example, be analyzed by using monobromobimane. Other known methods for analyzing the level of GSH in a cell can also be used. For example, the level of GSH can be analyzed by using Glutathione Assay Kit (catalog #703002) (Cayman Chemical, Ann Arbor, Mich.) For compounds that decrease the level of GSH, the method optionally further comprises the step of testing the compound in a cell assay using AML cell lines. Examples of AML cell lines include, but are not limited to, OCI-AML2, OCI-AML5, OCI-M2 and MV4-11 cell lines. The cell assay can be a cytotoxicity assay, an assay analyzing the mitochondrial membrane potential (MMP), an assay analyzing the level of ROS, or a combination thereof.

Another embodiment is directed to a method of identifying a compound for treating a subject with acute myeloid leukemia (AML) comprising testing the compound to determine whether the compound can dissipates mitochondrial membrane potential in a cancer cell. A compound that causes the dissipation of mitochondrial membrane potential in a cancer cell can be used for treating AML. The mitochondrial membrane potential in a cell can, for example, be analyzed by using DiIC1(5) (1,1',3,3,3',3'-hexamethylindodicarbocyanine iodide). Other known methods for analyzing the mitochondrial membrane potential in a cell can also be used. For example, the mitochondrial membrane potential can be analyzed by using Mitochondrial Membrane Potential Detection Kit (catalog #280002) (Stratagene, La Jolla, Calif.) For compounds that cause the dissipation of the mitochondrial membrane potential, the method optionally further comprises the step of testing the compound in a cell assay using AML cell lines. Examples of AML cell lines include, but are not limited to, OCI-AML2, OCI-AML5, OCI-M2 and MV4-11 cell lines. The cell assay can be a cytotoxicity assay, an assay analyzing the level of GSH, an assay analyzing the level of ROS, or a combination thereof.

In another embodiment, the method of identifying the compound for treating a subject with acute myeloid leukemia (AML) is as described in Example 2.

It has been surprisingly found that the transition metal chelate, coordinate or complex compounds disclosed herein show sufficient anti-cancer activity to make them suitable for monotherapies, as well as in combination or in co-therapies with other anti-proliferative or anticancer therapies. In particular, it has been found that transition metal chelates, coordinates or complexes of N-malonyl-bis(N'-methyl-N'-thiobenzoylhydrazide) or a prodrug, isomer, ester, salt, hydrate, solvate, polymorph or deprotonated form thereof, can have sufficient anti-cancer activity to make them suitable for monotherapies, as well as in combination or in co-therapies with other anti-proliferative or anticancer therapies such as paclitaxel.

Other anti-proliferative or anticancer therapies may be combined with the compounds or the pharmaceutical compositions of this invention to treat proliferative diseases and cancer. Examples include combination therapy with other anti-cancer drugs, surgery, radiotherapy (including, but not limited to, gamma-radiation, neutron beam radiotherapy, electron beam radiotherapy, proton therapy, brachytherapy, and systemic radioactive isotopes), thermal therapy (see, for example, U.S. Publication No. 2008/0119440) and endocrine therapy. Other anticancer agents that may be used in combination with the compounds or the pharmaceutical compositions of the present invention include biologic response modifiers (including, but not limited to, interferons, interleukins, and tumor necrosis factor (TNF)), hyperthermia and cryotherapy, agents to attenuate any adverse effects (e.g., antiemetics), and other approved chemotherapeutic drugs. Specific examples of anticancer agents are described in detail below. Preferably, the co-administered anti-cancer drug is an agent that stabilizes microtubules, such as paclitaxel or an analog of paclitaxel.

The compounds of the invention are advantageously in substantially pure form, e.g., greater than 50%, 60%, 70%, 80%, 90%, 95%, 97%, 99%, 99.5% or 99.9% pure by weight. "Percent purity by weight" means the weight of the compound divided by the weight of the compound plus impurities times 100%.

The compounds of the present invention can be prepared by reacting the bis[thiohydrazide amide] represented by Structural Formula (I) or a prodrug, isomer, ester, salt, hydrate, solvate, polymorph or a deprotonated form thereof with a transition metal salt. The transition metal salt can be any inorganic or organic salts of the transition metal cation. For example, chloride salt, nitrate salt, sulfate salt, acetate salt and the like can be reacted with a bis[thiohydrazide amide] or a prodrug, isomer, ester, salt, hydrate, solvate, polymorph or a deprotonated form thereof described herein to afford the compounds of the present invention. In one embodiment, the transition metal salt is a copper(II) salt, such as $CuCl_2$. In another embodiment, the transition metal salt is a nickel(H) salt, such as $NiCl_2.6H_2O$.

The ratio of the bis[thiohydrazide amide] and the transition metal cation source used is typically in the range of 0.5 to 2.0 or 0.8 to 1.2. In one embodiment, the ratio is about 1.

Solvents, such as methylene chloride, acetonitrile, acetone, alcohols (such as methanol, ethanol) tetrahydrofuran and water can be used in the reaction of the bis[thiohydrazide amide] derivative with the transition metal salts. In one embodiment, the solvent is ethanol.

The bis[thiohydrazide amides] used to prepare the disclosed compounds can be prepared according to methods described in U.S. Pat. Nos. 6,800,660, 6,762,204, and 6,825,235, and U.S. Publication No. 2008/0146842.

Certain compounds of the invention may be obtained as different isomers (e.g., stereoisomers, coordination isomers, linkage isomers, hydrate isomers, and the like). The invention includes isomeric forms of the disclosed compounds and both pure isomers and mixtures thereof, including racemic mixtures. Isomers can be separated and isolated using any suitable method, such as chromatography.

The compounds of the invention may contain one or more chiral centers and/or double bonds and, therefore, exist as stereoisomers, such as double-bond isomers (i.e., geometric isomers), enantiomers, or diastereomers. According to this invention, the chemical structures depicted herein, including the compounds of this invention, encompass all of the corresponding compounds' enantiomers, diastereomers and geometric isomers, that is, both the stereochemically pure form (e.g., geometrically pure, enantiomerically pure, or diastereomerically pure) and isomeric mixtures (e.g., enantiomeric, diastereomeric and geometric isomeric mixtures). In some cases, one enantiomer, diastereomer or geometric isomer will possess superior activity or an improved toxicity or kinetic profile compared to other isomers. In those cases, such enantiomers, diastereomers and geometric isomers of compounds of this invention are preferred.

The compounds of the invention or bis[thiohydrazide amide] described herein may be present in the form of salts. In one embodiment, the salts of the compounds of the invention refer to non-toxic "pharmaceutically acceptable salts." In another embodiment, the salts also include non-pharmaceutically acceptable salts, such as trifluoroacetate.

Pharmaceutically acceptable salt forms include pharmaceutically acceptable acidic/anionic or basic/cationic salts. Pharmaceutically acceptable acidic/anionic salts include, the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate, and triethiodide salts.

The compounds of the invention include pharmaceutically acceptable anionic salt forms, wherein the anionic salts include the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate, and triethiodide salts.

In co-therapy in combination with one or more other therapeutic agents (e.g., paclitaxel or paclitaxel analogs), the compound or the pharmaceutical composition disclosed herein can be administered simultaneously or separately with the other therapeutic agent(s). The exact details of the administration will depend on the pharmacokinetics of the two substances in the presence of each other, and can include administering two substances substantially at the same time, and one substance within a certain time period (e.g., within 24 hours) of administration of the other, if the pharmacokinetics are suitable. Designs of suitable dosing regimens are routine for one skilled in the art. In particular embodiments, two substances will be administered substantially simultaneously, i.e., within minutes of each other, or in a single composition that comprises both substances.

Suitable pharmaceutically acceptable carriers or diluents may contain inert ingredients which do not inhibit the biological activity of the compounds described herein. The pharmaceutically acceptable carriers or diluents should be biocompatible, i.e., non-toxic, non-inflammatory, non-immunogenic and devoid of other undesired reactions upon the administration to a subject. Standard pharmaceutical formulation techniques can be employed, such as those described in Remington's Pharmaceutical Sciences, Mack Publishing Company, Easton, Pa. Formulation of the compound to be administered will vary according to the route of administration selected (e.g., solution, emulsion, capsule). Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Methods for encapsulating compositions (such as in a coating of hard gelatin or cyclodextrins) are known in the art (see, e.g., Baker, et al., "Controlled Release of Biological Active Agents", John Wiley and Sons, 1986).

The compounds and pharmaceutical compositions disclosed herein is administered by any suitable route, including, for example, orally in capsules, suspensions or tablets or by parenteral administration. Parenteral administration can include, for example, systemic administration, such as by intramuscular, intravenous, subcutaneous, or intraperitoneal injection. The compound and pharmaceutical composition disclosed herein can also be administered orally (e.g., dietary), topically, by inhalation (e.g., intrabronchial, intranasal, oral inhalation or intranasal drops), or rectally, depending on the type of cancer to be treated. Oral and parenteral administrations are preferred modes of administration.

The present invention is illustrated by the following examples, which are not intended to be limiting in any way.

EXAMPLES

Example 1

Synthesis of the Compounds

Synthesis of Compound 1

Copper(II) chloride (277 mg, 2.0 mmol) was added to a solution of bis[thiohydrazide amide] A ("elesclomol", 800 mg, 2.0 mmol) in EtOH (10.0 mL). The mixture was stirred at room temperature for 20 minutes. Water was then added. The solid was collected by filtration. The solid was taken up in methylene chloride. The resulting solution was washed with water (2×), dried ($Na_2SO_4$), filtered and concentrated to give crude solid. The solid was washed with acetone to give the pure compound 1 (600 mg). Single crystal solid were obtained by recrystallization from acetonitrile. MS (ESI) [M+H$^+$]: 462. MP: 198-202° C. (decomposed). Anal. calc. For $C_{19}H_{18}CuN_4O_2S_2$: C, 49.39; H, 3.93; N, 12.13. found: C, 49.36; H, 3.68; N, 11.92.

| Table of Bond Distances in Armstrongs for Compound 1 | | |
|---|---|---|
| Atom 1 | Atom 2 | Distance |
| Cu1 | N7 | 1.944(2) |
| Cu1 | N3 | 1.948(2) |
| Cu1 | S1 | 2.2346(7) |
| Cu1 | S9 | 2.2375(7) |
| S1 | C1 | 1.694(3) |
| S9 | C9 | 1.707(3) |
| O4 | C4 | 1.231(3) |
| O6 | C6 | 1.227(3) |
| N2 | C1 | 1.321(3) |
| N2 | N3 | 1.405(3) |
| N2 | C21 | 1.482(3) |
| N3 | C4 | 1.370(3) |

Table of Bond Distances in Armstrongs for Compound 1

| Atom 1 | Atom 2 | Distance |
|---|---|---|
| N7 | C6 | 1.363(3) |
| N7 | N8 | 1.414(3) |
| N8 | C9 | 1.316(3) |
| N8 | C81 | 1.481(3) |
| C1 | C11 | 1.479(4) |
| C4 | C5 | 1.510(4) |
| C5 | C6 | 1.519(4) |
| C5 | H51 | 0.94(4) |
| C5 | H52 | 1.01(3) |
| C9 | C91 | 1.481(4) |
| C11 | C12 | 1.392(3) |
| C11 | C16 | 1.394(3) |
| C12 | C13 | 1.383(4) |
| C12 | H12 | 0.950 |
| C13 | C14 | 1.389(4) |
| C13 | H13 | 0.950 |
| C14 | C15 | 1.389(4) |
| C14 | H14 | 0.950 |
| C15 | C16 | 1.384(4) |
| C15 | H15 | 0.950 |
| C16 | H16 | 0.950 |
| C21 | H21A | 0.980 |
| C21 | H21B | 0.980 |
| C21 | H21C | 0.980 |
| C81 | H81A | 0.980 |
| C81 | H81B | 0.980 |
| C81 | H81C | 0.980 |
| C91 | C92 | 1.391(4) |
| C91 | C96 | 1.403(3) |
| C92 | C93 | 1.388(4) |
| C92 | H92 | 0.950 |
| C93 | C94 | 1.382(4) |
| C93 | H93 | 0.950 |
| C94 | C95 | 1.393(4) |
| C94 | H94 | 0.950 |
| C95 | C96 | 1.384(4) |
| C95 | H95 | 0.950 |
| C96 | H96 | 0.950 |

Numbers in parentheses are estimated standard deviations in the least significant digits.

Table of Bond Angles in Degrees for Compound 1

| Atom 1 | Atom 2 | Atom 3 | Angle |
|---|---|---|---|
| N7 | Cu1 | N3 | 96.27(8) |
| N7 | Cu1 | S1 | 161.69(6) |
| N3 | Cu1 | S1 | 86.92(6) |
| N7 | Cu1 | S9 | 86.58(6) |
| N3 | Cu1 | S9 | 158.38(6) |
| S1 | Cu1 | S9 | 97.10(3) |
| C1 | S1 | Cu1 | 96.53(9) |
| C9 | S9 | Cu1 | 96.97(9) |
| C1 | N2 | N3 | 118.7(2) |
| C1 | N2 | C21 | 122.7(2) |
| N3 | N2 | C21 | 116.67(19) |
| C4 | N3 | N2 | 112.6(2) |
| C4 | N3 | Cu1 | 118.96(18) |
| N2 | N3 | Cu1 | 115.96(14) |
| C6 | N7 | N8 | 113.3(2) |
| C6 | N7 | Cu1 | 120.48(17) |
| N8 | N7 | Cu1 | 116.52(14) |
| C9 | N8 | N7 | 118.6(2) |
| C9 | N8 | C81 | 123.2(2) |
| N7 | N8 | C81 | 115.93(19) |
| N2 | C1 | C11 | 120.7(2) |
| N2 | C1 | S1 | 121.3(2) |
| C11 | C1 | S1 | 118.07(17) |
| O4 | C4 | N3 | 125.2(2) |
| O4 | C4 | C5 | 119.7(2) |
| N3 | C4 | C5 | 114.9(2) |
| C4 | C5 | C6 | 124.5(2) |
| C4 | C5 | H51 | 111(2) |
| C6 | C5 | H51 | 106(2) |
| C4 | C5 | H52 | 101.6(19) |
| C6 | C5 | H52 | 111.1(19) |
| H51 | C5 | H52 | 99(3) |
| O6 | C6 | N7 | 125.4(2) |
| O6 | C6 | C5 | 118.8(2) |
| N7 | C6 | C5 | 115.6(2) |
| N8 | C9 | C91 | 121.6(2) |
| N8 | C9 | S9 | 120.7(2) |
| C91 | C9 | S9 | 117.68(18) |
| C12 | C11 | C16 | 119.6(2) |
| C12 | C11 | C1 | 119.8(2) |
| C16 | C11 | C1 | 120.5(2) |
| C13 | C12 | C11 | 119.7(2) |
| C13 | C12 | H12 | 120.20 |
| C11 | C12 | H12 | 120.20 |
| C12 | C13 | C14 | 120.7(3) |
| C12 | C13 | H13 | 119.60 |
| C14 | C13 | H13 | 119.60 |
| C13 | C14 | C15 | 119.6(3) |
| C13 | C14 | H14 | 120.20 |
| C15 | C14 | H14 | 120.20 |
| C16 | C15 | C14 | 119.9(2) |
| C16 | C15 | H15 | 120.00 |
| C14 | C15 | H15 | 120.00 |
| C15 | C16 | C11 | 120.4(2) |
| C15 | C16 | H16 | 119.80 |
| C11 | C16 | H16 | 119.80 |
| N2 | C21 | H21A | 109.50 |
| N2 | C21 | H21B | 109.50 |
| H21A | C21 | H21B | 109.50 |
| N2 | C21 | H21C | 109.50 |
| H21A | C21 | H21C | 109.50 |
| H21B | C21 | H21C | 109.50 |
| N8 | C81 | H81A | 109.50 |
| N8 | C81 | H81B | 109.50 |
| H81A | C81 | H81B | 109.50 |
| N8 | C81 | H81C | 109.50 |
| H81A | C81 | H81C | 109.50 |
| H81B | C81 | H81C | 109.50 |
| C92 | C91 | C96 | 119.1(2) |
| C92 | C91 | C9 | 121.6(2) |
| C96 | C91 | C9 | 119.1(2) |
| C93 | C92 | C91 | 120.6(2) |
| C93 | C92 | H92 | 119.70 |
| C91 | C92 | H92 | 119.70 |
| C94 | C93 | C92 | 120.1(3) |
| C94 | C93 | H93 | 119.90 |
| C92 | C93 | H93 | 119.90 |
| C93 | C94 | C95 | 119.8(3) |
| C93 | C94 | H94 | 120.10 |
| C95 | C94 | H94 | 120.10 |
| C96 | C95 | C94 | 120.5(2) |
| C96 | C95 | H95 | 119.80 |
| C94 | C95 | H95 | 119.80 |
| C95 | C96 | C91 | 119.9(3) |
| C95 | C96 | H96 | 120.00 |
| C91 | C96 | H96 | 120.00 |

Numbers in parentheses are estimated standard deviations in the least significant digits.

Synthesis of Compound 2

Compound 2 was prepared similarly as described for the preparation of compounds 1 using bis[thiohydrazide amide] A and nickel(II) chloride hexahydrate. MS (ESI) [M+H$^+$]: 457. $^1$H NMR (300 MHz, CDCl$_3$) δ 7.58-7.44 (m, 10H), 3.61 (s, 6H), 3.59 (s, 2H).

Example 2

Activity Against AML

Elesclomol induces apoptosis (programmed cell death) in cancer cells by disrupting cancer cell energy production and metabolism. Preclinical studies have shown that elesclomol acquires copper in the form of Cu$^{2+}$, from serum, and, once inside a cancer cell, enables the reduction reaction Cu(II) to Cu(I). This redox reaction disrupts mitochondrial respiration in cancer cells and elevates the level of reactive oxygen species (ROS) beyond sustainable levels, ultimately triggering the mitochondrial apoptosis pathway. This mechanism of action represents a novel way of selectively targeting and killing cancer cells.

Elesclomol is most effective under normoxic (normal oxygen) conditions where mitochondrial respiration is active. Under hypoxic (low-oxygen) conditions, energy production shifts to glycolysis in the cytoplasm and elesclomol anti-cancer activity is diminished. This shift is often associated with high LDH levels in the cell, and may be reflected by high levels in the serum as well. These observations are consistent with preliminary findings in a Phase 3 metastatic melanoma study ("SYMMETRY"), in which results showed a differential response to treatment with elesclomol based on level of baseline lactate dehydrogenase (LDH). The primary endpoint of progression-free survival improvement was achieved in the normal LDH population, with an acceptable safety profile. In the elevated LDH population, no difference was observed between the two arms of the trial for the primary endpoint, and a negative impact was observed for the survival endpoint.

Oxidative Stress as a Death Effector in AML

The respiratory chain is the most prominent source of cellular reactive oxygen generation, although many enzyme systems can contribute. Oxidative stress occurs when ROS production exceeds the capacity of cellular anti-oxidants. Glutathione (GSH) is the most abundant cellular anti-oxidant. Simultaneous monitoring of ROS production, GSH content, and mitochondrial membrane potential (MMP) is a powerful approach for studying the mechanisms of oxidative stress during apoptosis following treatment of AML blasts with Ara-C and g-radiation, and AML blasts are sensitized by the GSH-depleting agent BSO. Based on this, it was believed that AML blasts might be unusually sensitive to elesclomol, given the known ability of copper to catalyze ROS production via Fenton chemistry.

Elesclomol is an oxidative stress inducer that triggers apoptosis in cancer cells. In laboratory studies, elesclomol binds copper in plasma, facilitates its uptake into cells, and enables a transition between copper oxidation states once inside the cell. Elesclomol has been observed to increase the high level of ROS in cancer cells even further, leading to an increase in pro-apoptotic factors, a decrease in anti-apoptotic factors, the opening of the mitochondrial membrane pores, and ultimately to the initiation of programmed cell death via the mitochondrial apoptosis pathway. This mechanism of action, called oxidative stress induction, represents a novel way of selectively targeting and killing cancer cells. In preclinical models elesclomol showed potent anti-cancer activity against a broad range of cancer cell types, as well as an ability to enhance the efficacy of certain chemotherapy agents with minimal additional toxicity. In the clinic, the drug has been administered in clinical trials to >600 subjects, most recently in the Phase 3 SYMMETRY trial for metastatic melanoma.

Materials and Methods

Cell lines: OCI-AML2, OCI-AML5, OCI-M2 (p53 mutant M6), MV4-11 (FLT3-ITD)

Patients were treated by the Princess Margaret Hospital Leukemia Program.

Primary blasts from 10 AML patients isolated by density gradient or RBC lysis, maintained in a-MEM+10% FBS±10% 5637-conditioned medium.

Flow Cytometry Protocol:
Combined staining at 37° for:
MMP—DiIC1(5) 40 nM 30'
ROS—carboxy-dichlorofluorescin 5 mM or dihydrorhodamine 123 1 mM for 30'
GSH—monobromobimane 40 mM for 5'
Surface membrane integrity—propidium iodide 1 mg/ml for 5'
Samples run on 3 laser flow cytometer (Gallios, Beckman-Coulter)

Figure 1:
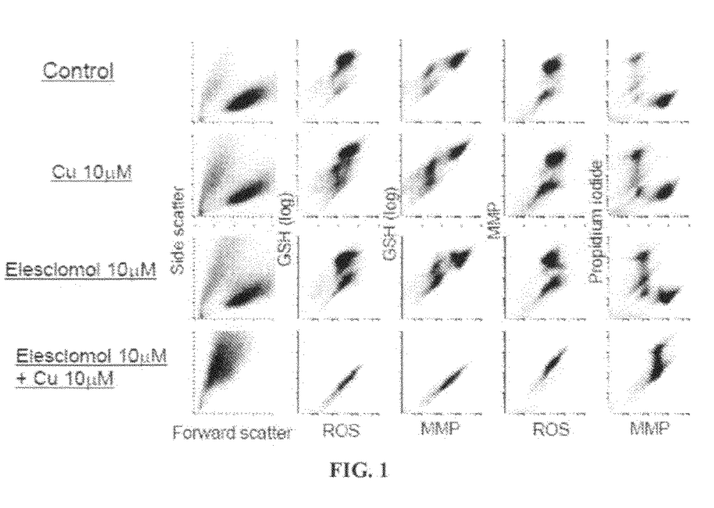
FIG. 1 shows the effects of elesclomol and elesclomol-Cu (II) on OCI-AML2 cells.
Figure 2:
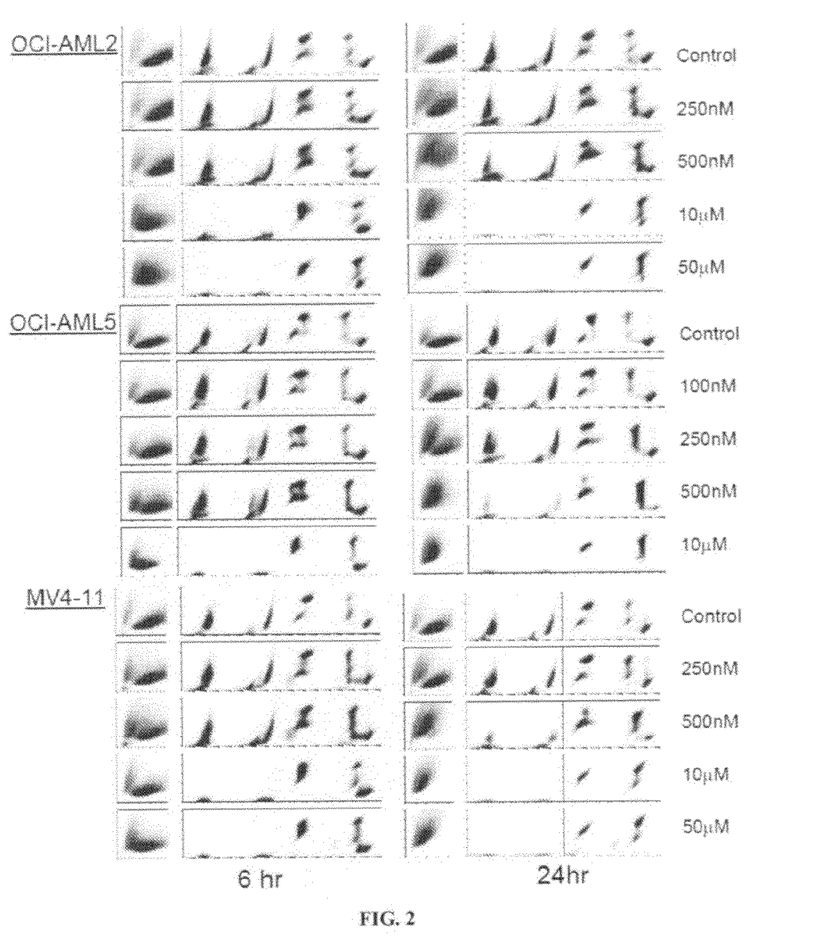
FIG. 2 shows the effect of elesclomol-Cu(II) on GSH depletion and mitochondrial membrane depolarization in AML cell lines
Figure 3A:
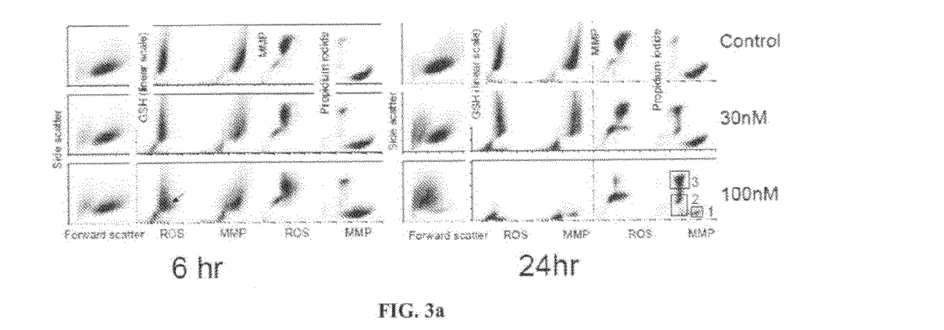
FIGS. 3a-3d show the effect of elesclomol-Cu(II) on AML patient blast cells.

The effects of elesclomol and elesclomol-Cu(II) on OCI-AML2 cells are seen in FIG. 1. The effect of elesclomol-Cu (II) on GSH depletion and mitochondrial membrane depolarization in AML cell lines is seen in FIG. 2. The potent effect of elesclomol-Cu(II) on AML patient blast cells is seen in FIGS. 3a-3d. In FIG. 3a, patient #123, the dual MMP/PI plots show that loss of mitochondrial membrane potential precedes the loss of outer membrane integrity (numbered boxes, bottom right panel). Reduced GSH is lost co-incident with the loss of MMP. The pattern is similar to that seen in AML cell lines, but the primary patient blasts are more drug-sensitive. There is a slight increase in ROS seen in the sample treated with 100nM elesclomol-Cu(II) for 6 hr (arrowed), but not an overall increase in ROS in this case.

Figure 3B:
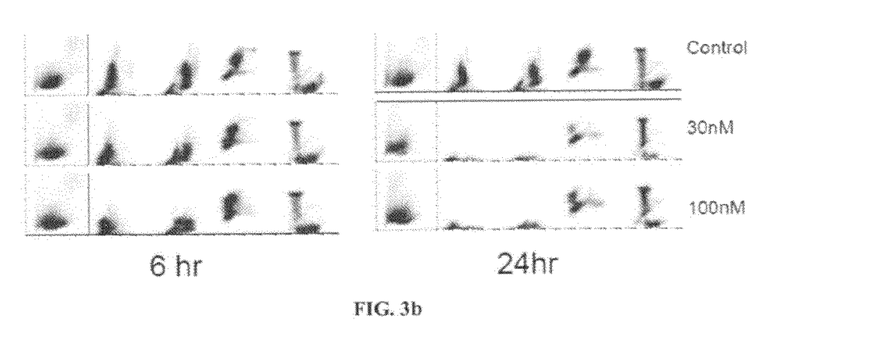

In FIG. 3b, Patient #127, the pattern is similar to Patient #123, although the baseline GSH level is lower, and this example shows loss of GSH following exposure to 30 nM elesclomol-Cu(II), which is already evident at 6 hr.

Figure 3C:
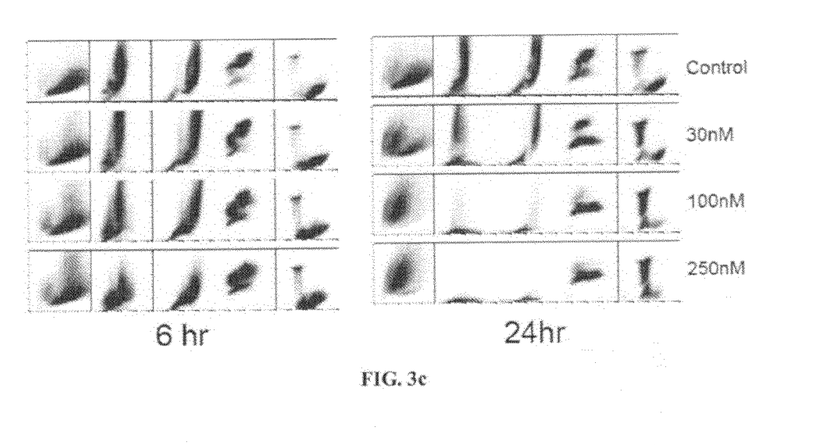

In FIG. 3c, Patient #131, the overall pattern is similar to the other two cases, with a loss of GSH co-incident with loss of MMP and increased ROS (which is most evident at the 30 nM 24 hr point). Blasts have higher baseline GSH and are less sensitive to elesclomol-Cu(II).

Figure 3D:
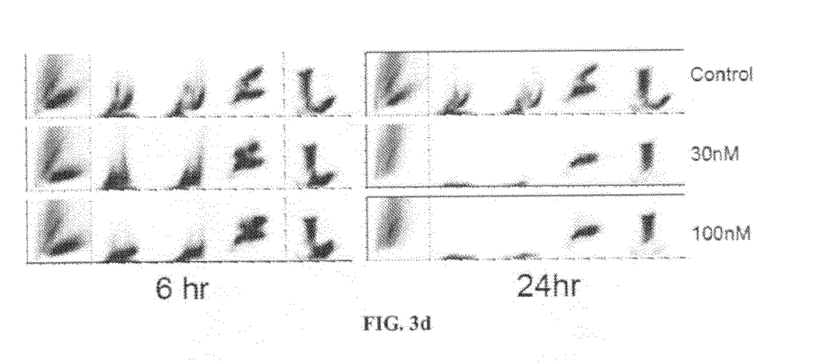

In FIG. 3d, Patient #126, shows a more heterogeneous distribution of GSH and ROS at baseline, but is also highly sensitive to elesclomol-Cu(II).

It can thus be seen that ex vivo elesclomol treatment of primary blast cells isolated from patients with AML showed that the drug rapidly induced mitochondrial dysfunction and cell death. Importantly, the primary blasts were highly sensitive to the drug, with all samples exhibiting significant impairment at 30 nM elesclomol-Cu(II), a concentration that is well below the presumed serum concentrations in subjects. The depletion of GSH and dissipation of mitochondrial membrane potential occurred in all cases; consistent with previously reported effects of copper toxicity on glutathione metabolism.

Example 3

Treatment of Patients with AML

A Phase I clinical trial will characterize the safety and tolerability of elesclomol sodium administered to subjects with relapsed or refractory acute myeloid leukemia (AML); and determine the pharmacokinetics of elesclomol and elesclomol metabolites (including elesclomol-Cu++) in subjects with relapsed or refractory AML. Other objectives include determining an optimal Phase II dose and schedule for elesclomol sodium in subjects with AML; evaluating peripheral blood response to the administration of elesclomol (efficacy based on complete blood count) in relapsed or refractory AML; and correlating mitochondrial membrane potential with biological effect of elesclomol.

The study is a multiple-dose, dose-escalation study, with once-weekly dosing of elesclomol sodium to determine the maximum tolerated dose (MTD). A "3+3" dose escalation design will be used. Additional subjects may be enrolled at the MTD if the sponsor and investigators agree that additional data would support evaluation of secondary and exploratory objectives. Based on prior clinical experience, 200 mg/m$^2$ was selected as the starting dose.

The diagnosis and main criteria for inclusion include:
1. Age≥18 years
2. Cytologically confirmed Acute Myeloid Leukemia that meets at least one of the following:
   Has relapsed after the completion of induction and/or consolidation therapy
   Has failed to respond to standard induction therapy
3. Life expectancy≥3 months
4. Acceptable organ and marrow function during the screening period as defined by:
   Total bilirubin<1.5 times the ULN
   Aspartate aminotransferase (AST)≤2.5 times ULN
   Alanine aminotransferase (ALT)≤2.5 times ULN
   Serum creatinine≤1.5×ULN
   LDH (total)≤0.8×ULN Eligible subjects will receive elesclomol sodium via a 60 minute infusion once per week until discontinuation of treatment due to progressive disease or other reasons. If a dose-limiting toxicity (DLT) is seen in any of the three (3) subjects at any dose level, up to three (3) more subjects will be enrolled at the same dose level.

Blood samples will be obtained from all subjects enrolled in each cohort for the determination of pharmacokinetics of elesclomol and metabolites (including elesclomol-Cu++) in plasma. Data from this pharmacokinetic analysis may also be used to determine appropriate dosing for further development.

Efficacy will be assessed based on bone marrow aspirate at Cycle 1, Day 29. Response will be assessed as defined by Cheson, B. D. *Revised Recommendations of the International Working Group for Diagnosis, Standardization of Response Criteria, Treatment Outcomes, and Reporting Standards for Therapeutic Trials in Acute Myeloid Leukemia* J. Clin. Onc. 2003 21:4642-4649.

Clinical safety assessments will include the number, severity, and treatment association of AEs (serious and non-serious), changes from baseline in physical examination findings, vital sign measurements, concomitant medications, and ECG tracings.

While this invention has been particularly shown and described with references to example embodiments thereof, it will be understood by those skilled in the art that various changes in form and details may be made therein without departing from the scope of the invention encompassed by the appended claims.

All publications, patent applications, patents, and other documents cited herein are incorporated by reference in their entirety. In case of conflict, the present specification, including definitions, will control. In addition, the materials, methods, and examples are illustrative only and not intended to be limiting in any way.

What is claimed is:

1. A method of treating a subject with acute myeloid leukemia, comprising administering to the subject an effective amount of a bis[thio-hydrazide amide]-related compound, wherein the subject has LDH (total) ≤0.8 ×ULN, wherein the bis[thio-hydrazide amide]-related compound is a salt or a disalt of a compound represented by the following Structural Formula:

2. The method of claim 1, wherein the bis[thio-hydrazide amide]-related compound is a bis[thiohydrazide amide] or a deprotonated form thereof complexed to a transition metal cation, represented by the following Structural Formula:

3. The method of claim 2, wherein the transition metal cation is $Ni^{2+}$, $Cu^{2+}$, $Co^{2+}$, $Fe^{2+}$, $Zn^{2+}$, $Pt^{2+}$ or $Pd^{2+}$.

4. The method of claim 3, wherein the transition metal cation is $Cu^{2+}$.

5. The method of claim 2, wherein the molar ratio of bis[thiohydrazide amide] or deprotonated form thereof to transition metal cation is equal to or greater than 0.5 and equal to or less than 2.0.

6. The method of claim 5, wherein the molar ratio of bis[thiohydrazide amide] or deprotonated form thereof to transition metal cation is 1:1.

7. The method of claim 1, wherein the bis[thio-hydrazide amide]-related compound is a compound represented by the following structural formula:

wherein X is a transition metal cation with a +2 charge.

8. The method of claim 7, wherein the compound is greater than 50% pure by weight.

9. The method of claim 7, wherein the compound is greater than 90% pure by weight.

10. The method of claim 9, wherein X is $Ni^{2+}$, $Cu^{2+}$, $Co^{2+}$, $Fe^{2+}$, $Zn^{2+}$, $Pt^{2+}$ or $Pd^{2+}$.

11. The method of claim 9, wherein X is $Cu^{2+}$.

12. The method of claim 1, further comprising treating the subject with γ-radiation.

13. The method of claim 1, further comprising treating the subject with cytarabine and γ-radiation.

14. The method of claim 1, wherein the acute myeloid leukemia is relapsed or refractory acute myeloid leukemia.

* * * * *